US008999311B2

(12) United States Patent
De La Poterie (10) Patent No.: US 8,999,311 B2
(45) Date of Patent: Apr. 7, 2015

(54) COSMETIC COMPOSITION HAVING A CERTAIN THERMAL PROFILE (75) Inventor: Valérie De La Poterie, le Chatelet en Brie (FR)

(73) Assignee: Air Products and Chemicals, Inc., Allentown, PA (US)

( * ) Notice: Subject to any disclaimer, the term of this patent is extended or adjusted under 35 U.S.C. 154(b) by 1345 days.

(21) Appl. No.: 10/821,919

(22) Filed: Apr. 12, 2004

(65) Prior Publication Data

US 2005/0013838 A1 Jan. 20, 2005

Related U.S. Application Data (60) Provisional application No. 60/496,925, filed on Aug. 22, 2003.

(30) Foreign Application Priority Data

Apr. 11, 2003 (FR) ...................................... 03 04593
Apr. 17, 2003 (FR) ...................................... 03 04825

(51) Int. Cl.
A61Q 1/10 (2006.01)
A61Q 5/06 (2006.01)
A61K 8/81 (2006.01)
A45D 40/26 (2006.01)

(52) U.S. Cl.
CPC ................ A61Q 5/06 (2013.01); A61K 8/8152 (2013.01); A61Q 1/10 (2013.01); A45D 40/265 (2013.01); A45D 2200/155 (2013.01); A45D 2200/157 (2013.01); A61K 2800/54 (2013.01)

(58) Field of Classification Search
None
See application file for complete search history.

(56) References Cited

U.S. PATENT DOCUMENTS

| 3,911,105 | A | * | 10/1975 | Papantoniou et al. | .......... 424/64 |
| 5,156,911 | A | | 10/1992 | Stewart | |
| 5,498,407 | A | | 3/1996 | Atlas | |
| 5,519,063 | A | | 5/1996 | Mondet et al. | |
| 5,736,125 | A | | 4/1998 | Morawsky et al. | |
| 5,775,344 | A | | 7/1998 | Clay | |
| 5,849,278 | A | * | 12/1998 | Piot et al. | ..................... 424/70.7 |
| 5,851,517 | A | | 12/1998 | Mougin et al. | |
| 5,853,010 | A | | 12/1998 | Suh | |
| 5,856,653 | A | | 1/1999 | Boudreaux | |
| 5,866,111 | A | | 2/1999 | Felardos et al. | |
| 5,882,635 | A | * | 3/1999 | Ramin et al. | .................... 424/61 |
| 5,945,095 | A | | 8/1999 | Mougin et al. | |
| 6,009,884 | A | | 1/2000 | Suh | |
| 6,082,918 | A | | 7/2000 | Gueret | |
| 6,180,123 | B1 | | 1/2001 | Mondet | |
| 6,220,252 | B1 | | 4/2001 | Heintz | |
| 6,254,877 | B1 | | 7/2001 | De La Poterie et al. | |
| 6,682,748 | B1 | | 1/2004 | De La Poterie et al. | |
| 6,875,245 | B2 | * | 4/2005 | Pavlin | ............................. 44/275 |
| 6,946,518 | B2 | | 9/2005 | De La Poterie | |
| 6,949,504 | B2 | | 9/2005 | Mondet et al. | |
| 7,029,662 | B2 | | 4/2006 | Auguste et al. | |
| 7,129,276 | B2 | * | 10/2006 | Ferrari | ........................ 514/772.3 |
| 7,255,870 | B2 | * | 8/2007 | Lennon et al. | ................ 424/401 |
| 2001/0018484 | A1 | | 8/2001 | Bitler et al. | |
| 2002/0197220 | A1 | | 12/2002 | Mondet et al. | |
| 2003/0003154 | A1 | | 1/2003 | De La Poterie | |
| 2003/0059389 | A1 | | 3/2003 | Tournilhac et al. | |
| 2005/0123493 | A1 | * | 6/2005 | Ferrari et al. | ................... 424/63 |

FOREIGN PATENT DOCUMENTS

| EP | 0 931 476 | | 7/1999 |
| FR | 2824263 | * | 11/2002 |
| WO | WO 99/22782 | | 5/1999 |
| WO | WO 00/74519 A2 | | 12/2000 |
| WO | WO 01/19333 A1 | | 3/2001 |
| WO | WO 01/78551 | | 10/2001 |

OTHER PUBLICATIONS

Shuichi Nojima et al., "Melting Behavior of Poly(ε-caprolactone)-block-Polybutadiene Copolymers," Macromolecules, vol. 32, No. 11, pp. 3727-3734 (1999).
B. Boutevin et al., "Study of morphological and mechanical properties of PP/PBT blends," Polymer Bulletin, vol. 34, No. 1, pp. 117-123 (1995).
Pratima Rangarajan et al., "Morphology of Semicrystalline Block Copolymers of Ethylene-(Ethylene-alt- propylene)," Macromolecules, vol. 26, No. 17, pp. 4640-4645 (1993).
D. Richter et al., "Polymer Aggregates with Crystalline Cores: The System Polyethylene-Poly(ethylenepropylene)," Macromolecules, vol. 30, pp. 1053-1068 (1997).
I.W. Hamley, "Crystallization in Block Copolymers," Advances in Polymer Science, vol. 148, pp. 113-137 (1999).
Kirk-Othmer, "Encyclopedia of Chemical Technology," Third Edition, vol. 22, John Wiley & Sons, pp. 332-432 (1983).
Copending U.S. Appl. No. 10/821,920, filed Apr. 12, 2004.
English language Abstract of EP 0 931 476, dated Jul. 28, 1999.
English language Abstract of EP 0 928 607, dated Jul. 14, 1999.
English language Abstract of FR 2 827 167, dated Jan. 17, 2003.
English language Abstract of JP 2000-038314, dated Feb. 8, 2000.
English language Abstract of WO 03/007899, dated Jan. 30, 2003.

(Continued)

Primary Examiner — Jyothsna Venkat
(74) Attorney, Agent, or Firm — Finnegan, Henderson, Farabow, Garrett & Dunner, LLP (57) ABSTRACT The present disclosure relates to a cosmetic composition comprising, in a physiologically acceptable medium, at least one compound which gives the cosmetic composition a thermal profile having a melting peak wherein the mid-height width Lf is less than or equal to 20° C., and wherein the composition is heat-stable. The present disclosure also relates to the process of depositing a film on the keratin fibers, wherein the film is homogenous and/or has improved curling properties, comprising applying the cosmetic composition disclosed herein to keratin fibers.

16 Claims, 2 Drawing Sheets

(56) References Cited

OTHER PUBLICATIONS

French Search Report for FR 03/04571, dated Nov. 21, 2003, which is a French Priority Application for co-pending U.S. Appl. No. 10/821,920.
French Search Report for FR 03/04825, dated Mar. 15, 2004, which is a French Priority Application for co-pending U.S. Appl. No. 10/821,920.
French Search Report for FR 03/51146, dated Jun. 24, 2004, which is a French Priority Application for co-pending U.S. Appl. No. 10/821,920.
Office Action mailed Feb. 3, 2009, in co-pending U.S. Appl. No. 10/821,920.
Office Action mailed Mar. 21, 2008, in co-pending U.S. Appl. No. 10/821,920.
Office Action mailed Sep. 3, 2008, in co-pending U.S. Appl. No. 10/821,920.
U.S. Appl. No. 12/837,239, filed Jul. 15, 2010.
Office Action mailed Jun. 17, 2009, in co-pending U.S. Appl. No. 10/821,920.

\* cited by examiner

COSMETIC COMPOSITION HAVING A CERTAIN THERMAL PROFILE

This application claims benefit of U.S. Provisional Application No. 60/496,925, filed Aug. 22, 2003.

The present disclosure relates to a cosmetic composition having a thermal profile with a melting peak whose mid-height width (Lf) is less than or equal to 20° C., such as less than or equal to 10° C.

The cosmetic composition according to the present disclosure may be, for example, a cosmetic composition for coating keratin fibers such as human eyelashes, eyebrows and hair, or alternatively false eyelashes. The present disclosure also relates to a process for making up or caring for keratin materials.

The cosmetic composition as disclosed herein may be a makeup composition, such as a mascara, a makeup base for keratin fibers, or basecoat, a composition to be applied over a makeup, also known as a topcoat, or a composition for treating keratin fibers. For instance, the composition according to the present disclosure may be a mascara.

"Curling" mascara compositions comprising a mixture of waxes and of film-forming polymer are known, such as the compositions described in document EP-B-0 928 607.

The use of organogelling agents in mascara compositions that may replace all or some of the waxes in order to possibly obtain improved curling properties of the eyelashes is also known from document WO 00/74519.

However, such compositions do not allow optimum curling of the eyelashes.

Moreover, devices exist that may assist the curling the eyelashes, such as "eyelash curlers." One type of eyelash curler consists, for example, in pinching the eyelashes between the jaws of a clip to give them a curled shape before applying the makeup, but this operation can be difficult to perform.

Other eyelash curlers can be in the form of a heating clip or a heating brush, as described in U.S. Pat. No. 5,853,010 or JP 2000-38314, to shape the eyelash by the action of heat. These heating instruments may be applied to naked eyelashes, but the curling effect obtained may be poor, or to eyelashes coated with any mascara composition. When the heating instruments are used with pre-coated eyelashes, it is common for some of the composition coating the eyelashes to be removed by the action of the heat, and/or for the cosmetic properties of this composition to be degraded. For example, the composition film may lose its homogeneity, and the eyelashes can become stuck together, which results in an unattractive makeup result on the keratin fibers.

The aim of the present inventor was to provide a cosmetic composition for coating keratin fibers that can allow improved curling of the eyelashes, for example, by the action of heat, and may have at least one good cosmetic property chosen from uniform deposition and good curling behavior over time.

This cosmetic composition may be used for instance, in combination with a heating instrument, such as a heating brush, which may be applied to the eyelashes before, during or after they have been coated with the composition, or conditioned in a device for applying the composition while hot.

The inventor has discovered, surprisingly, that a mascara having at least one of the good cosmetic properties described above may be obtained by using a composition with a thermal profile as disclosed herein.

For example, disclosed herein is a cosmetic composition comprising:

i) a physiologically acceptable medium, and ii) at least one compound which gives the cosmetic composition a thermal profile having a melting peak whose mid-height width Lf is less than or equal to 20° C., wherein the composition is heat-stable.

The term "physiologically acceptable medium" means a non-toxic medium that can be applied to keratin fibers, such as human eyelashes, eyebrows and hair, and which is, for instance, compatible with the region of the eyes.

The term "heat-stable" denotes a composition with a viscosity that varies by no more than 25%, for instance, no more than 20%, such as no more than 15% and for example, no more than 10%, after being subjected to a succession of X number of cycles of melting/cooling according to the following protocol: the composition is placed in an oven at 80° C. for 2 hours. The composition is then allowed to return naturally to room temperature. An interval of 24 hours is left between 2 successive cycles, and the viscosity after performing the X number of cycles is measured. The viscosity measured after performing the X number of melting/cooling cycles is compared with that measured before the first cycle.

In one embodiment, X=4, such as, X=8, for instance, X=10, and for further example, X=15.

On account of this heat-stability characteristic, the cosmetic properties of the composition disclosed herein may not be substantially impaired by the temperature changes experienced when it is subjected to a source of heat.

Another aspect of the present disclosure is a method of coating keratin fibers in order to deposit on the keratin fibers a film which is homogeneous and/or which has improved curling properties. The method comprises applying to the keratin fibers a cosmetic composition comprising:

i) a physiologically acceptable medium, and ii) at least one compound that gives the cosmetic composition a thermal profile having a melting peak with a mid-height width Lf less than or equal to 20° C., wherein the cosmetic composition is heat-stable.

Still another aspect of the present disclosure is a non-therapeutic cosmetic process for making up or caring for keratin fibers, comprising the application to the keratin fibers of a composition as defined above.

Yet another aspect of the present disclosure is a non-therapeutic cosmetic process for making up or caring for keratin materials, such as the skin, the lips or keratin fibers, comprising the application to the keratin materials of a cosmetic composition as described herein, wherein the composition is, prior to, simultaneously with or subsequent to its application, brought to a temperature above or equal to its melting point, m.p., for example, above or equal to its end melting temperature Tf.

The composition may be brought to a temperature above or equal to its melting point prior to its application, for example, by heating with microwaves or with a water bath, or by any other heating means equipping a packaging and application assembly containing it, for instance, the walls of a reservoir containing the composition. Alternatively, the composition may be brought to a temperature above or equal to its melting point simultaneously with or subsequent to its application, for instance, using an application device with heating means, such as a heating brush.

DETERMINATION OF THE THERMAL PROFILE OF THE COMPOSITION

The thermal profile of the composition according to the present disclosure is determined using a differential scanning calorimeter (DSC), for example the calorimeter sold under the name DSC 30 by the company Mettler.

A sample of 5 to 10 mg of product placed in a crucible is subjected to a first temperature increase ranging from −20° C. to 90° C., at a heating rate of 5° C./minute; it is then cooled from 90° C. to −20° C. at a cooling rate of 5° C./minute and is finally subjected to a second temperature increase ranging from −20° C. to 90° C. at a heating rate of 5° C./minute. During the second temperature increase, the variation of the difference in power absorbed by the empty crucible and by the crucible containing the sample of product is measured as a function of the temperature.

The thermal profile of the composition as disclosed herein shows a narrow melting peak, which for example has a mid-height peak width Lf of less than or equal to 20° C., such as ranging from 0.5° C. to 20° C., for instance from 1° C. to 10° C., for example, ranging from 2° C. to 5° C. The mid-height of the melting peak may be determined on the basis of the half-distance between a straight line connecting two flat portions of the thermal profile on either side of the melting peak, and the top of the peak.

The melting peak may also have a melting point m.p. ranging from 20° C. to 80° C., for example, ranging from 25° C. to 75° C., such as from 35° C. to 60° C. The melting point of the peak that is considered is the temperature value corresponding to the top of the peak of the curve representing the variation of the difference in power absorbed as a function of the temperature.

The melting peak may for example, have a low temperature amplitude $\Delta T = Tf - To$ of less than or equal to 30° C., such as ranging from 1° C. to 30° C., for instance, from 2° C. to 25° C., for example ranging from 3° C. to 20° C., To being the starting melting temperature corresponding to the temperature measured when 5% of the heat of fusion is consumed and Tf being the end melting temperature, which corresponds to the temperature measured when 95% of the heat of fusion has been consumed.

For instance, the starting melting temperature To of the composition may be greater than or equal to 10° C., ranging, for example, from 10° C. to 50° C., such as greater than or equal to 15° C., for example ranging from 15° C. to 45° C., and for instance, greater than or equal to 20° C., for example ranging from 20° C. to 40° C.

For further example, the end melting temperature of the composition Tf may be less than or equal to 90° C., such as ranging from 35° C. to 90° C., for instance less than or equal to 80° C., for example ranging from 40° C. to 80° C., such as less than or equal to 70° C., for example ranging from 40° C. to 70° C., and for instance, ranging from 40 to 60° C.

Compositions having the characteristics described herein, for example, a low amplitude $\Delta T$, have the feature, when they are heated to a temperature above their melting point m.p., such as to a temperature above or equal to their end melting temperature (Tf), of passing from a supple or soft state (temperature above m.p.) to a semi-rigid, i.e., semi-crystalline state (temperature below m.p.) in a very short space of time.

Accordingly, it is possible to shape eyelashes coated with such a composition by the action of a source of heat, such as a heating brush, with a temperature above or equal to the melting point of the composition, and to do so quickly.

For example, the thermal profile of the cosmetic composition according to the present disclosure may have a single melting peak. For further example, the at least one compound giving the cosmetic composition a thermal profile with a melting peak with a mid-height width Lf less than or equal to 20° C., may itself have a thermal profile with a melting peak whose mid-height width Lf is less than or equal to 20° C. The at least one compound for instance, may be chosen from waxes, polymers, for example semi-crystalline polymers, and oils thickened with a structuring agent.

The at least one compound may be present in the cosmetic composition in an amount ranging from 1% to 60%, such as from 3% to 55%, for instance from 5% to 50%, and for example, from 10% to 40% by weight, relative to the total weight of the composition.

In the present disclosure, a wax is a lipophilic compound, which is solid at room temperature, i.e., about 25° C., with a reversible solid/liquid change of state, and which has a melting point of greater than or equal to 30° C. that may be up to 120° C. By bringing the wax to the liquid state, i.e., melting, it is possible to make it miscible with oils and to form a microscopically homogeneous mixture, but upon returning the temperature of the mixture to room temperature, recrystallization of the wax in the oils of the mixture can be obtained.

The melting point of the wax may be measured using a differential scanning calorimeter (DSC), for example the calorimeter sold under the name DSC 30 by the company Mettler. A 15 mg sample of product placed in a crucible is subjected to a first temperature rise ranging from 0° C. to 120° C., at a heating rate of 10° C./minute, and is then cooled from 120° C. to 0° C. at a cooling rate of 10° C./minute, and is then subjected to a second temperature rise ranging from 0° C. to 120° C. at a heating rate of 5° C./minute. During the second temperature rise, the variation in the difference in power absorbed by the empty crucible and by the crucible containing the sample of product is measured as a function of the temperature. The melting point of the compound is the value of the temperature corresponding to the top of the peak of the curve representing the variation of the difference in power absorbed as a function of the temperature.

The waxes that may be used in the cosmetic composition according to the present disclosure may be chosen from waxes that are solid and rigid at room temperature, of animal, plant, mineral or synthetic origin, and mixtures thereof. The waxes may have a melting point ranging from about 30° C. to about 80° C., such as ranging from 30° C. to 70° C., and for instance ranging from 35° C. to 65° C.

For example, the wax may be chosen from olive wax obtained by hydrogenation of olive oil esterified with stearyl alcohol, such as the wax Phytowax Olive 18L57 (melting point m.p.=58.6° C.) sold by the company Sophim; stearyl alcohol (melting point m.p.=60° C.); stearyl stearate (melting point m.p.=57° C.); stearyl benzoate (melting point m.p.=40° C.); bis(trimethylolpropane)tetrastearate (melting point m.p.=46° C.); the wax Licowax KST (polyethoxylated fatty acids of Montan wax) from the company Clariant (melting point m.p.=55° C.); bis(trimethylolpropane)tetrabehenate (melting point m.p.=67.5° C.); dioctadecyl carbonate wax (melting point m.p.=57° C.); and mixtures thereof.

The composition according to the present disclosure may comprise a polymer. For example, the polymer may be a semi-crystalline polymer. The term "semi-crystalline polymer" means polymers comprising at least one crystallizable portion, chosen from crystallizable pendent chains and crystallizable blocks, in the skeleton, as well as an amorphous portion in the skeleton, and having a first-order reversible temperature of change of phase, such as of melting (solid-liquid transition). When the crystallizable portion of the polymer is in the form of a crystallizable block of the polymer skeleton, the amorphous portion of the polymer is in the form of an amorphous block; the semi-crystalline polymer is, in this case, a block copolymer, for example, of the diblock, triblock or multiblock type, comprising at least one crystallizable block and at least one amorphous block. The term "block" generally means at least five identical repeating units. The at least one crystallizable block is then of a different chemical nature from the at least one amorphous block.

The at least one semi-crystalline polymer that may be used in the cosmetic composition as disclosed herein has a melting point of greater than or equal to 20° C., such as ranging from 20° C. to 80° C., for example, ranging from 30° C. to 70° C., and for instance from 35° C. to 65° C. This melting point is a first-order temperature of change of phase. The melting point may be measured by any known method, for example, using a differential scanning calorimeter (DSC) as described above.

According to one aspect of the present disclosure, the at least one semi-crystalline polymer as disclosed herein may have a number-average molecular mass of greater than or equal to 1000. For example, the at least one semi-crystalline polymer as disclosed herein may have a number-average molecular mass $\overline{Mn}$ ranging from 2,000 to 800,000, such as from 3,000 to 500,000, for instance, from 4000 to 150,000, such as less than 100,000 and for example from 4,000 to 99,000. For further example, the at least one semi-crystalline polymer may have a number-average molecular mass of greater than 5,600, such as ranging from 5,700 to 99,000.

For the purposes of the present disclosure, the expression "crystallizable chain or block" means a chain or block which, if it were obtained alone, would change from the amorphous state to the crystalline state reversibly, depending on whether the block is above or below the melting point. For the purposes of the present disclosure, a "chain" is a group of atoms, which are pendent or lateral relative to the polymer skeleton. A "block" is a group of atoms belonging to the skeleton. For instance, the "pendent crystallizable chain" may be a chain comprising at least 6 carbon atoms.

The crystallizable blocks or chains of the semi-crystalline polymers may be present in the polymer in an amount, for example, of at least 30% of the total weight of each polymer, such as at least 40% of the total weight of each polymer. The semi-crystalline polymers of the present disclosure that comprise crystallizable blocks are thus block or multiblock polymers. They may be obtained by polymerizing a monomer containing reactive, e.g. ethylenic, double bonds or by polycondensation. When the polymers of the present disclosure are polymers comprising crystallizable side chains, these side chains may be, for example, in random or statistical form.

The semi-crystalline polymers that may be used in the composition as disclosed herein, may be for example of synthetic origin. Moreover, they do not comprise a polysaccharide skeleton. In general, the crystallizable units, i.e., chains or blocks, of the semi-crystalline polymers of the present disclosure originate from at least one monomer comprising crystallizable blocks or chains, used for the manufacture of the semi-crystalline polymers.

Among the semi-crystalline polymers that may be used in the cosmetic composition according to the present disclosure, non-limiting mention may be made of, for example:

block copolymers of polyolefins with controlled crystallization, for instance those whose monomers are described in EP-A-0 951,897, polycondensates, for instance of aliphatic or aromatic polyester type or of aliphatic/aromatic copolyester type, homopolymers or copolymers bearing at least one crystallizable side chain and homopolymers or copolymers bearing at least one crystallizable block in the skeleton, for instance those described in U.S. Pat. No. 5,156,911, homopolymers or copolymers bearing at least one crystallizable side chain, for instance comprising fluoro group(s), as described in document WO-A-01/19333, and mixtures thereof.

With respect to the last two types of polymers, the at least one crystallizable side chain or block is hydrophobic.

Semi-Crystalline Polymers Comprising Crystallizable Side Chains

Among the semi-crystalline polymers comprising crystallizable side chains, non-limiting mention may be made for example, of those defined in U.S. Pat. No. 5,156,911 and in WO-A-01/19333. These polymers may be homopolymers or copolymers comprising from 50% to 100% by weight of units resulting from the polymerization of at least one monomer bearing a crystallizable hydrophobic side chain. These homopolymers or copolymers may be of any nature, provided that they meet the conditions of the present disclosure. They may result from:

the polymerization, for instance, the free-radical polymerization, of at least one monomer comprising at least one reactive or ethylenic double bond with respect to a polymerization, such as a vinyl, (meth)acrylic or allylic group, the polycondensation of at least one monomer bearing co-reactive groups, e.g., carboxylic acid, sulphonic acid, alcohol, amine and isocyanate, such as, for example, polyesters, polyurethanes, polyethers, polyureas and polyamides.

In general, these polymers may be chosen from, for example, homopolymers and copolymers resulting from the polymerization of at least one monomer comprising at least one crystallizable chain of formula (I):

wherein M is an atom of the polymer skeleton, S is a spacer and C is a crystallizable group.

The crystallizable chains "—S—C" may be aliphatic or aromatic, and optionally fluorinated or perfluorinated. For example, S may be chosen from $(CH_2)_n$, $(CH_2CH_2O)_n$, and $(CH_2O)$, which may be linear, branched, or cyclic, wherein n is an integer ranging from 0 to 22. For instance, S may be a linear group. For further example, S and C may be different from each other.

When the crystallizable chains "—S—C" are hydrocarbon-based aliphatic chains, they may comprise hydrocarbon-based alkyl chains containing at least 11 carbon atoms and not more than 40 carbon atoms, such as not more than 24 carbon atoms. They may be, for example, aliphatic chains or alkyl chains comprising at least 12 carbon atoms, for example, $C_{14}$-$C_{24}$ alkyl chains. When they are fluoroalkyl or perfluoroalkyl chains, they comprise at least six fluorinated carbon atoms, such as at least 11 carbon atoms wherein at least six of the carbon atoms are fluorinated.

As examples of semi-crystalline polymers or copolymers comprising at least one crystallizable chain, non-limiting mention may be made of those resulting from the polymerization of at least one of the following monomers: (meth)acrylates of saturated alkyl with the alkyl group being $C_{14}$-$C_{24}$; perfluoroalkyl(meth)acrylates with a $C_{11}$-$C_{15}$ perfluoroalkyl group; N-alkyl(meth)acrylamides with the alkyl group ranging from $C_{14}$ to $C_{24}$ optionally with a fluorine atom; vinyl esters comprising alkyl or perfluoro(alkyl) chains with the alkyl group ranging from $C_{14}$ to $C_{24}$ with at least 6 fluorine atoms per perfluoroalkyl chain; vinyl ethers comprising alkyl or perfluoro(alkyl) chains with the alkyl group ranging from $C_{14}$ to $C_{24}$ with at least 6 fluorine atoms per perfluoroalkyl chain; $C_{14}$ to $C_{24}$ alpha-olefins such as, for example, octadecene; para-alkylstyrenes with an alkyl group comprising from 12 to 24 carbon atoms, and mixtures thereof.

When the polymers result from a polycondensation, the hydrocarbon-based and/or fluorinated crystallizable chains as defined above are borne by a monomer chosen from diacids, diols, diamines and diisocyanate.

When the polymers are copolymers, they may additionally comprise from 0 to 50% of groups Y or Z resulting from the copolymerization of Y or Z, wherein Y may be chosen from polar and non-polar monomers or a mixture of the two.

When Y is a polar monomer, it may be either a monomer bearing polyoxyalkylenated groups, such as oxyethylenated and/or oxypropylenated groups; a hydroxyalkyl(meth)acrylate, for instance hydroxyethyl acrylate; (meth)acrylamide; an N-alkyl(meth)acrylamide; an N,N-dialkyl(meth)acrylamide such as, for example, N,N-diisopropylacrylamide or N-vinylpyrrolidone (NVP); N-vinylcaprolactam; a monomer bearing at least one carboxylic acid group, for instance (meth)acrylic acid, crotonic acid, itaconic acid, maleic acid and fumaric acid; or a monomer bearing a carboxylic acid anhydride group, for instance maleic anhydride, and mixtures thereof.

When Y is a non-polar monomer, it may be an ester of the linear, branched or cyclic alkyl(meth)acrylate type, a vinyl ester, an alkyl vinyl ether, an alpha-olefin, styrene or styrene substituted with a $C_1$ to $C_{10}$ alkyl group, for instance α-methylstyrene, or a macromonomer of the polyorganosiloxane type containing vinyl unsaturation.

For the purposes of the present disclosure only, the term "alkyl" means a saturated group, for example, ranging from $C_8$ to $C_{24}$, such as from $C_{14}$ to $C_{24}$, except where noted otherwise.

Z may be a polar monomer or a mixture of polar monomers. Z has the same definition as that of Y when it is polar, as defined above.

The semi-crystalline polymers comprising at least one crystallizable side chain may be, for example, chosen from alkyl(meth)acrylate and alkyl(meth)acrylamide homopolymers with an alkyl group as defined above, for instance, ranging from $C_{14}$-$C_{24}$; copolymers of these monomers with a hydrophilic monomer for example, of different nature from (meth)acrylic acid, for instance N-vinylpyrrolidone and hydroxyethyl(meth)acrylate; and mixtures thereof.

Semi-Crystalline Polymers Bearing in the Skeleton at Least One Crystallizable Block The polymers comprising at least one crystallizable block in the skeleton may be chosen from, for example, block copolymers comprising at least two blocks of different chemical nature, one of which is crystallizable. Among such polymers, non-limiting mention may be made of:

the block polymers defined in U.S. Pat. No. 5,156,911;

block copolymers of olefin or of cycloolefin comprising a crystallizable chain, for instance those derived from the block polymerization of:

cyclobutene, cyclohexene, cyclooctene, norbornene, i.e. bicyclo(2,2,1)-2-heptene, 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene, and mixtures thereof, with ethylene, propylene, 1-butene, 3-methyl-1-butene, 1-hexene, 4-methyl-1-pentene, 1-octene, 1-decene, 1-eicosene, and mixtures thereof.

For example, copoly(ethylene/norbornene) blocks and (ethylene/propylene/ethylidene-norbornene) block terpolymers may be used. For further example, the block polymers resulting from the block copolymerization of at least two $C_2$-$C_{16}$, such as $C_2$-$C_{12}$, for instance $C_4$-$C_{12}$ α-olefins such as those mentioned above and for instance block bipolymers of ethylene and of 1-octene may also be used.

The copolymers may be copolymers comprising at least one crystallizable block, wherein the copolymer residue is amorphous at room temperature. These copolymers may also comprise two crystallizable blocks of different chemical nature. For example, copolymers may simultaneously comprise at room temperature a crystallizable block and an amorphous block that are both hydrophobic and lipophilic, sequentially distributed; non-limiting mention may be made, for example, of polymers comprising at least one crystallizable block and at least one amorphous block chosen from:

blocks crystallizable by nature, chosen from polyester, for instance poly(alkylene terephthalate), and polyolefin, for instance polyethylenes and polypropylenes, and amorphous and lipophilic blocks chosen from amorphous polyolefins and copoly(olefin)s such as poly(isobutylene), hydrogenated polybutadiene and hydrogenated poly(isoprene).

As examples of such copolymers comprising a crystallizable block and a separate amorphous block, non-limiting mention may be made of:

poly(ε-caprolactone)-b-poly(butadiene) block copolymers, for instance used in hydrogenated form, such as those described in the article "Melting behaviour of poly(ε-caprolactone)-block-polybutadiene copolymers" from S. Nojima, Macromolecules, 32, 3727-3734 (1999);

the hydrogenated block or multiblock polybutylene terephthalate)-b-poly(isoprene) block copolymers cited in the article "Study of morphological and mechanical properties of PP/PBT" by B. Boutevin et al., Polymer Bulletin, 34, 117-123 (1995);

the poly(ethylene)-b-copoly(ethylene/propylene) block copolymers cited in the articles "Morphology of semi-crystalline block copolymers of ethylene-(ethylene-alt-propylene)" by P. Rangarajan et al., Macromolecules, 26, 4640-4645 (1993) and "Polymer aggregates with crystalline cores: the system poly(ethylene)-poly(ethylene-propylene)" by P. Richter et al., Macromolecules, 30, 1053-1068 (1997);

the poly(ethylene)-b-poly(ethylethylene) block copolymers cited in the general article "Crystallization in block copolymers" by I. W. Hamley, Advances in Polymer Science, Vol. 148, 113-137 (1999).

The semi-crystalline polymers in the composition of the present disclosure may optionally be partially crosslinked, provided that the degree of crosslinking does not interfere with their dissolution or dispersion, when heated above their melting point, in the liquid fatty phase optionally present in the composition. The crosslinking may be a chemical crosslinking, by reaction with a multifunctional monomer during the polymerization. It may also be a physical crosslinking which may, in this case, be due either to the establishment of bonds of hydrogen or dipolar type between groups borne by the polymer, such as, for example, the dipolar interactions between carboxylate ionomers, these interactions being of small amount and borne by the polymer skeleton; or due to a phase separation between the crystallizable blocks and the amorphous blocks borne by the polymer. For example, the semi-crystalline polymers in the composition disclosed herein may be non-crosslinked.

According to one aspect of the present disclosure, the polymer may be chosen from copolymers resulting from the polymerization of at least one monomer comprising a crystallizable chain chosen from saturated $C_{14}$ to $C_{24}$ alkyl(meth)acrylates; $C_{11}$ to $C_{15}$ perfluoroalkyl(meth)acrylates; $C_{14}$ to $C_{24}$ N-alkyl(meth)acrylamides optionally comprising a fluorine atom; vinyl esters comprising $C_{14}$ to $C_{24}$ alkyl or perfluoroalkyl chains; vinyl ethers comprising $C_{14}$ to $C_{24}$ alkyl or perfluoroalkyl chains, $C_{14}$ to $C_{24}$ alpha-olefins; and para-alkylstyrenes with an alkyl group comprising from 12 to 24 carbon atoms, with at least one optionally fluorinated $C_1$ to $C_{10}$ monocarboxylic acid ester or amide of formula (II):

wherein $R_1$ is chosen from H and $CH_3$, R is chosen from optionally fluorinated $C_1$-$C_{10}$ alkyl groups, and X is chosen from O, NH and $NR_2$ wherein $R_2$ is chosen from optionally fluorinated $C_1$-$C_{10}$ alkyl groups.

According to another aspect of the present disclosure, the polymer may be derived from a monomer comprising a crystallizable chain, chosen from saturated $C_{14}$ to $C_{22}$ alkyl(meth)acrylates.

As examples of the semi-crystalline polymers that may be used in the composition according to the present disclosure, non-limiting mention may be made of the products Intelimer® from the company Landec, described in the brochure "Intelimer®polymers", Landec IP22 (Rev. 4-97). These polymers are in solid form at room temperature, i.e., about 25° C. These polymers also bear crystallizable side chains and have the formula (I) above.

The semi-crystalline polymers may also be, for example, chosen from those described in Examples 3, 4, 5, 7, 9 and 13 of U.S. Pat. No. 5,156,911 comprising a —COOH group, resulting from the copolymerization of acrylic acid and of $C_5$ to $C_{16}$ alkyl(meth)acrylate, such as from the copolymerisation of:

acrylic acid, hexadecyl acrylate and isodecyl acrylate in a 1/16/3 weight ratio,
acrylic acid and pentadecyl acrylate in a 1/19 weight ratio,
acrylic acid, hexadecyl acrylate and ethyl acrylate in a 2.5/76.5/20 weight ratio,
acrylic acid, hexadecyl acrylate and methyl acrylate in a 5/85/10 weight ratio,
acrylic acid and octadecyl methacrylate in a 2.5/97.5 weight ratio,
hexadecyl acrylate, polyethylene glycol methacrylate monomethyl ether comprising 8 ethylene glycol units, and acrylic acid in an 8.5/1/0.5 weight ratio.

It is also possible to use the structure "O" from National Starch, a methacrylic acid/octadecyl acrylate (5/85) copolymer with a melting point of 44° C., described in U.S. Pat. No. 5,736,125, and also semi-crystalline polymers with crystallizable pendent chains comprising fluoro groups, as described in Examples 1, 4, 6, 7 and 8 of WO-A-01/19333.

It is also possible to use alkyl(meth)acrylate copolymers comprising polydimethylsiloxane grafts, such as the stearyl acrylate copolymer comprising polydimethylsiloxane grafts (melting point of about 30° C.) or the behenyl acrylate copolymer comprising polydimethylsiloxane grafts (melting point of about 49° C.), which are sold by the company Shin-Etsu under the respective names KP-561 and KP 562 (CTFA name: acrylates/dimethicone).

The semi-crystalline polymers having a low melting point, which are obtained by copolymerization of stearyl acrylate and of acrylic acid or of NVP, as described in U.S. Pat. No. 5,519,063 or EP-A-550,45, may also be used.

The semi-crystalline polymers obtained by copolymerization of behenyl acrylate and of acrylic acid or of NVP, as described in U.S. Pat. No. 5,519,063 and EP-A-550,745, may also be used.

In one aspect of the present disclosure, the semi-crystalline polymers do not comprise a carboxyl group.

The cosmetic composition as disclosed herein may also comprise an oil or an oil thickened with a structuring agent.

In the case where the cosmetic composition comprises waxes and/or semi-crystalline polymers as described above, these polymers may act as structuring agents. The structuring agent may also be chosen from the lipophilic gelling agents conventionally used in cosmetics.

The term "oil" means a fatty substance that is liquid at room temperature, i.e., about 25° C., and atmospheric pressure, i.e., 760 mmHg, or 105 Pa).

The oil may be chosen from any physiologically acceptable and for example, cosmetically acceptable oils, such as mineral, animal, plant and synthetic oils; for instance, volatile or non-volatile hydrocarbon-based and/or silicone and/or fluoro oils, and mixtures thereof. More specifically, as disclosed herein, the term "hydrocarbon-based oil" means an oil mainly comprising carbon and hydrogen atoms and optionally at least one functional group chosen from hydroxyl, ester, ether and carboxylic groups. Generally, the oil may have a viscosity ranging from 0.5 to 100 000 cps, such as from 50 to 50 000 cps, and for instance, from 100 to 300 000 cps.

As examples of oils that may be used in the present disclosure, non-limiting mention may be made of:

hydrocarbon-based oils of animal origin, such as perhydrosqualene;

hydrocarbon-based plant oils such as liquid triglycerides of fatty acids ranging from 4 to 24 carbon atoms, for instance heptanoic or octanoic acid triglyceride, or alternatively sunflower oil, maize oil, soybean oil, marrow oil, grapeseed oil, sesame seed oil, hazelnut oil, apricot oil, macadamia oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter;

linear or branched hydrocarbons of mineral or synthetic origin, such as liquid paraffin and derivatives thereof, petroleum jelly, polydecenes, polybutenes and hydrogenated polyisobutene, such as parleam;

synthetic esters and ethers, such as of fatty acids, for instance the oils of formula $R_1COOR_2$ wherein $R_1$ is chosen from higher fatty acid residues comprising from 1 to 40 carbon atoms and $R_2$ is chosen from hydrocarbon-based chains comprising from 1 to 40 carbon atoms, wherein $R_1+R_2 \geq 10$; for instance purcellin oil, isononyl isononanoate, isopropyl myristate, 2-ethylhexyl palmitate, 2-octyldodecyl stearate, 2-octyldodecyl erucate, isostearyl isostearate or tridecyl trimellitate; hydroxylated esters, for instance isostearyl lactate, octyl hydroxystearate, octyldodecyl hydroxystearate, diisostearyl malate, triisocetyl citrate and fatty alkyl heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate;

fatty alcohols comprising from 12 to 26 carbon atoms, for instance octyldodecanol, 2-butyloctanol, 2-hexyldecanol, 2-undecylpentadecanol or oleyl alcohol;

fluoro oils, optionally partially hydrocarbon-based and/or silicone-based;

silicone oils, for instance volatile or non-volatile, linear or cyclic polydimethylsiloxanes (PDMSs); polydimethylsiloxanes comprising alkyl, alkoxy or phenyl groups, which may be pendent or at the end of a silicone chain, these groups comprising from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenyl ethyl trimethyl siloxysilicates; and mixtures thereof.

Among lipophilic gelling agents conventionally used in cosmetics, examples that may be given non-limiting mentioned include mineral lipophilic gelling agents such as clays or silicas, polymeric organic lipophilic gelling agents such as partially or totally crosslinked elastomeric organopolysiloxanes, block copolymers, of the poly-styrene/copoly(ethylene-propylene) type, polyamides, and mixtures thereof.

The cosmetic composition according to the present disclosure may be in the form of an aqueous or anhydrous continuous phase, or in the form of a water-in-oil or oil-in-water emulsion, or a water-in-oil or oil-in-water dispersion.

The total fatty phase of the composition, formed from the wax and/or the polymer, for example, with the semi-crystalline polymer, and/or the oil thickened with a structuring agent and an additional fatty substance, may be present in the composition in an amount ranging from 0.1% to 60% by weight, for instance, ranging from 0.5% to 50% by weight, such as ranging from 1% to 40% by weight, relative to the total weight of the composition.

The cosmetic composition as disclosed herein may also comprise an aqueous phase, which may consist essentially of water. It may also comprise a mixture of water and of water-miscible solvent, for instance lower monoalcohols comprising from 1 to carbon atoms, such as ethanol or isopropanol, glycols comprising from 2 to 8 carbon atoms, such as propylene glycol, ethylene glycol, 1,3-butyleneglycol or dipropylene glycol, $C_3$-$C_4$ ketones and $C_2$-$C_4$ aldehydes. The aqueous phase, i.e., water and optionally at least one water-miscible organic solvent, may be present in the composition in an amount ranging from 5% to 95% by weight, relative to the total weight of the composition.

The aqueous phase of the cosmetic composition may be thickened with a thickener. Among the aqueous-phase thickeners that may be used according to the present disclosure, non-limiting mention may be made of cellulose-based thickeners, clays, polysaccharides, acrylic polymers, associative polymers, and mixtures thereof.

In the cosmetic composition as disclosed herein, the aqueous-phase thickener may be present in an amount ranging from 0.1% to 15% by weight, such as from 1% to 10%, for instance from 1% to 5% by weight, relative to the total weight of the composition.

The cosmetic composition may also comprise nonionic, anionic, cationic or amphoteric surfactants, or alternatively emulsifying surfactants. Reference may be made to the document "Encyclopaedia of Chemical Technology, Kirk-Othmer", Volume 22, pp. 333-432, 3rd edition, 1979, Wiley, for the definition of the properties and emulsifying functions of surfactants, for example pp. 347-377 of the reference, for the anionic, amphoteric and nonionic surfactants.

The cosmetic composition according to the present disclosure may further comprise at least one dyestuff, for instance pulverulent dyestuffs, liposoluble dyes and water-soluble dyes. The at least one dyestuff may be present in an amount ranging from 0.1% to 20% by weight, for example, ranging from 1% to 15% by weight, relative to the total weight of the composition.

The pulverulent dyestuffs may be chosen from pigments and nacres. The pigments may be chosen from white, colored, mineral organic, coated and uncoated pigments. Among the mineral pigments, non-limiting mention may be made of titanium dioxide optionally surface-treated, zirconium oxide, zinc oxide and cerium oxide, as well as iron oxide, chromium oxide, manganese violet, ultramarine blue, chromium hydrate and ferric blue. Among the organic pigments, non-limiting mention may be made of carbon black, pigments of D & C type, and lakes based on cochineal carmine or on barium, strontium, calcium and aluminium.

The nacres may be chosen from white nacreous pigments such as mica coated with titanium or with bismuth oxychloride, colored nacreous pigments such as titanium mica with iron oxides, titanium mica with, for example, ferric blue or chromium oxide, titanium mica with an organic pigment of the abovementioned type, and nacreous pigments based on bismuth oxychloride.

The liposoluble dyes may be, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes may be, for example, beetroot juice or methylene blue.

The cosmetic composition according to the present disclosure may also comprise at least one additional polymer that is a film-forming polymer.

The at least one film-forming polymer may be a polymer that is made soluble or is dispersed in the form of solid particles in an aqueous phase of the composition, or may be dissolved or dispersed in the form of solid particles in a liquid fatty phase. The composition may comprise a blend of these polymers. When the film-forming polymer is in the form of solid particles, these particles may have a mean particle size ranging from 5 nm to 600 nm, such as from 20 nm to 300 nm.

The at least one film-forming polymer may be present in the composition as disclosed herein in a solids content amount ranging from 0.1% to 60% by weight, such as from 0.5% to 40% by weight, for example, from 1% to 30% by weight, relative to the total weight of the composition.

As used herein, the term "film-forming" means a polymer capable of forming, by itself or in the presence of an auxiliary film-forming agent, a continuous film that adheres to a support, for instance, to keratin materials. Among the film-forming polymers that may be used in the composition as disclosed herein, non-limiting mention may be made of synthetic polymers of radical-mediated type or of polycondensate type, polymers of natural origin, and mixtures thereof.

The expression "radical-mediated film-forming polymer" means a polymer obtained by polymerization of monomers containing unsaturation, fir example, ethylenic unsaturation, each monomer being capable of homopolymerizing, unlike polycondensates.

The film-forming polymers of radical-mediated type may be, for example, vinyl polymers or copolymers, such as acrylic polymers. The vinyl film-forming polymers can result from the polymerization of monomers containing ethylenic unsaturation and comprising at least one acidic group and/or esters of these acidic monomers and/or amides of these acidic monomers.

Monomers bearing an acidic group which may be used include α,β-ethylenic unsaturated carboxylic acids such as acrylic acid, methacrylic acid, crotonic acid, maleic acid and itaconic acid. For example, (meth)acrylic acid and crotonic acid may be used. In one aspect of the present disclosure, (meth)acrylic acid is used.

The esters of acidic monomers may be chosen from (meth) acrylic acid esters, also known as (meth)acrylates, for instance (meth)acrylates of an alkyl, such as of a $C_1$-$C_{30}$ for example, $C_1$-$C_{20}$ alkyl, (meth)acrylates of an aryl, for instance, of a $C_6$-$C_{10}$ aryl, and (meth)acrylates of a hydroxyalkyl, such as of a $C_2$-$C_6$ hydroxyalkyl.

Among the alkyl(meth)acrylates that may be used, non-limiting mention may be made of methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl(meth)acrylates that may be used, non-limiting mention may be made of hydroxyethyl acrylate, 2-hydroxypropyl acrylate, hydroxyethyl methacrylate and 2-hydroxypropyl methacrylate.

Among the aryl(meth)acrylates that may be used, non-limiting mention may be made of benzyl acrylate and phenyl acrylate.

For example, the (meth)acrylic acid esters used may be alkyl(meth)acrylates.

The alkyl group of the esters may be either fluorinated or perfluorinated, i.e. some or all of the hydrogen atoms of the alkyl group may be substituted with fluorine atoms.

Examples of amides of the acid monomers that may be mentioned are (meth)acrylamides, such as N-alkyl(meth) acrylamides, for instance of a $C_2$-$C_{12}$ alkyl. Among the N-alkyl(meth)acrylamides that may be used, non-limiting mention may be made of N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. For example, these monomers may be polymerized with acid monomers and/or esters thereof and/or amides thereof, such as those mentioned above.

Among examples of vinyl esters that may be used, non-limiting mention may be made of vinyl acetate, vinyl neodecanoate, vinyl pivalate, vinyl benzoate and vinyl t-butylbenzoate.

Non-limiting examples of styrene monomers that may be mentioned include styrene and α-methylstyrene.

It is possible to use any monomer known to those skilled in the art that falls within the categories of acrylic and vinyl monomers, including monomers modified with a silicone chain.

Among the film-forming polycondensates that may be used, non-limiting mention may be made of polyurethanes, polyesters, polyesteramides, polyamides, epoxyester resins and polyureas.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea/polyurethanes, and mixtures thereof.

The polyesters may be obtained, in a known manner, by polycondensation of dicarboxylic acids with polyols, such as diols.

The dicarboxylic acid may be aliphatic, alicyclic or aromatic. Non-limiting examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acid monomers may be used alone or as a combination of at least two dicarboxylic acid monomers. For example, the dicarboxylic monomers may be chosen from phthalic acid, isophthalic acid and terephthalic acid.

The diol may be chosen from aliphatic, alicyclic and aromatic diols. The diol used may be, for example, chosen from: ethylene glycol, diethylene glycol, triethylene glycol, 1,3-propanediol, cyclohexanedimethanol and 4-butanediol. Other polyols that may be used are glycerol, pentaerythritol, sorbitol and trimethylolpropane.

The polyesteramides may be obtained in a manner analogous to that of the polyesters, by polycondensation of diacids with diamines or amino alcohols. Diamines that may be used include ethylenediamine, hexamethylenediamine and meta- or para-phenylenediamine. An amino alcohol that may be used is monoethanolamine.

The polyester may also comprise at least one monomer bearing at least one group —$SO_3M$, wherein M may be chosen from hydrogen atoms, ammonium ions $NH_4^+$ and metal ions, such as, for example, $Na^+$, $Li^+$, $K^+$, $Mg^{2+}$, $Ca^{2+}$, $Cu^{2+}$, $Fe^{2+}$ and $Fe^{3+}$ ions. A difunctional aromatic monomer comprising at least one group —$SO_3M$ may be used, for example.

The aromatic nucleus of the difunctional aromatic monomer comprising at least one group —$SO_3M$ as described above may be chosen, for example, from benzene, naphthalene, anthracene, biphenyl, oxybiphenyl, sulphonylbiphenyl and methylenebiphenyl nuclei. As examples of difunctional aromatic monomers also comprising at least one group —$SO_3M$, non-limiting mention may be made of: sulphoisophthalic acid, sulphoterephthalic acid, sulphophthalic acid, and 4-sulphonaphthalene-2,7-dicarboxylic acid.

Among the copolymers that may be used, non-limiting mention may be made of those based on isophthalate/sulphoisophthalate, such as copolymers obtained by condensation of diethylene glycol, cyclohexanedimethanol, isophthalic acid and sulphoisophthalic acid. Such polymers are sold, for example, under the brand name Eastman AQ® by the company Eastman Chemical Products.

The polymers of natural origin, optionally modified, may be chosen from shellac resin, sandarac gum, dammar resins, elemi gums, copal resins, cellulose polymers, and mixtures thereof.

According to a first aspect of the cosmetic composition as disclosed herein, the at least one film-forming polymer may be present in the form of particles dispersed in an aqueous phase, which is generally known as a latex or pseudolatex. The techniques for preparing these dispersions are well known to those skilled in the art.

Aqueous dispersions of film-forming polymers that may be used include the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins; Dow Latex 432® by the company Dow Chemical; Daitosol 5000 AD® by the company Daito Kasey Kogyo; Syntran 5760, Syntran 5190 and Syntran 5170 sold by the company Interpolymer; or the aqueous dispersions of polyurethane sold under the names Neorez R-981® and Neorez R-974® by the company Avecia-Neoresins; Avalure UR-405®, Avalure UR-410®, Avalure UR-425®, Avalure UR-450®, Sancure 875®, Sancure 861®, Sancure 878® and Sancure 2060® by the company Goodrich; Impranil 85® by the company Bayer and Aquamere H-1511® by the company Hydromer. Aqueous dispersions of film-forming polymers that may also be used include the polymer dispersions resulting from the free-radical polymerization of at least one free-radical monomers inside and/or partially at the surface of pre-existing particles of at least one polymer chosen from polyurethanes, polyureas, polyesters, polyesteramides and alkyd polymers. These polymers are generally referred to as hybrid polymers.

According to a second aspect of the composition as disclosed herein, the at least one film-forming polymer may be a water-soluble polymer and is thus present in the aqueous phase of the composition in dissolved form. Non-limiting examples of water-soluble film-forming polymers that may be mentioned include:

proteins, for instance proteins of plant origin such as wheat proteins and soybean proteins; proteins of animal origin such as keratins, for example keratin hydrolysates and sulphonic keratins;

anionic, cationic, amphoteric or nonionic chitin or chitosan polymers;

polymers of cellulose such as hydroxyethylcellulose, hydroxypropylcellulose, methylcellulose, ethylhydroxyethylcellulose and carboxymethylcellulose, and quaternized cellulose derivatives;

acrylic polymers or copolymers, such as polyacrylates or polymethacrylates, for example the sodium polymethacrylate manufactured or sold by the company Vanderbilt under the commercial reference Darvan 7;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol; and polymers of natural origin, which may be optionally modified, such as:

gum arabics, guar gum, xanthan derivatives, karaya gum;

alginates and carrageenans;

glycosaminoglycans, hyaluronic acid and derivatives thereof;

shellac resin, sandarac gum, dammar resins, elemi gums and copal resins;

deoxyribonucleic acid;

mucopolysaccharides such as hyaluronic acid and chondroitin sulphates, and mixtures thereof.

According to another aspect of the composition as disclosed herein, the at least one film-forming polymer may be present in a liquid fatty phase comprising organic oils or solvents. For the purposes of the present disclosure, the expression "liquid fatty phase" means a fatty phase which is liquid at room temperature, i.e., about 25° C., and atmospheric pressure, i.e., 760 mm Hg or $10^5$ Pa, composed of at least one fatty substance that is liquid at room temperature, also known as oils, which are generally mutually compatible. The liquid fatty phase may comprise, for example, a volatile oil, optionally mixed with a non-volatile oil, the oils possibly being chosen from those mentioned above.

According to still another aspect of the composition as disclosed herein, the at least one film-forming polymer may be present in the form of surface-stabilized particles dispersed in the liquid fatty phase. The dispersion of surface-stabilized polymer particles may be manufactured as described in EP-A-749,747.

The polymer particles are surface-stabilized by means of a stabilizer, which may be a block polymer, a grafted polymer and/or a random polymer, alone or as a mixture.

Dispersions of film-forming polymer in the liquid fatty phase, in the presence of stabilizers, are described for example, in EP-A-749,746, EP-A-923,928 and EP-A-930,060, the content of which is incorporated into the present disclosure by reference.

The size of the polymer particles in dispersion either in the aqueous phase or in the liquid fatty phase may range from 5 nm to 600 nm, such as from 20 nm to 300 nm.

According to yet another aspect of the composition as disclosed herein, the at least one film-forming polymer may be dissolved in the liquid fatty phase, in which case the film-forming polymer is said to be a liposoluble polymer.

Non-limiting examples of liposoluble polymers that may be mentioned are copolymers of vinyl ester, wherein the vinyl group is directly linked to the oxygen atom of the ester group and the vinyl ester comprises a saturated, linear or branched hydrocarbon-based radical of 1 to 19 carbon atoms, linked to the carbonyl of the ester group, and of at least one other monomer which may be chosen from vinyl esters other than the vinyl ester already present, α-olefins comprising from 8 to 28 carbon atoms, alkyl vinyl ethers wherein the alkyl group comprises from 2 to 18 carbon atoms, and allylic and methallylic esters comprising a saturated, linear or branched hydrocarbon-based radical of 1 to 19 carbon atoms, linked to the carbonyl of the ester group.

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Non-limiting examples of the copolymers that may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetaallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Non-limiting examples of liposoluble film-forming polymers that may also be mentioned include liposoluble homopolymers, such as those resulting from the homopolymerization of vinyl esters comprising from 9 to 22 carbon atoms or of alkyl acrylates or methacrylates, and alkyl radicals comprising from 10 to 20 carbon atoms.

Such liposoluble homopolymers may be chosen from polyvinyl stearate; polyvinyl stearate crosslinked with the aid of divinylbenzene, of diallyl ether or of diallyl phthalate; polystearyl(meth)acrylate; polyvinyl laurate and polylauryl(meth)acrylate, it being possible for these poly(meth)acrylates to be crosslinked with the aid of ethylene glycol dimethacrylate or tetraethylene glycol dimethacrylate.

The liposoluble homopolymers and copolymers defined above are known and are described for example in patent application FR-A-2,262,303; they may have a weight-average molecular weight ranging from 2000 to 500 000, such as from 4000 to 200 000.

As liposoluble film-forming polymers which may be used in accordance with the present disclosure, non-limiting mention may also be made of polyalkylenes, for instance, copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) and for example, copolymers of vinylpyrrolidone and of $C_2$ to $C_{40}$ and for instance, $C_3$ to $C_{20}$ alkene. As examples of VP copolymers which may be used as disclosed herein, non-limiting mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene and VP/acrylic acid/lauryl methacrylate.

The cosmetic composition according to the present disclosure may comprise an auxiliary film-forming agent that promotes the formation of a film with the at least one film-forming polymer. Such a film-forming agent may be chosen from any compound known to those skilled in the art as being capable of satisfying the desired function, such as plasticizers and coalescers.

The cosmetic composition of the present disclosure may also comprise at least one additive usually used in cosmetics, such as antioxidants, preserving agents, fragrances, neutralizers, plasticizers, cosmetic active agents, for instance emollients, moisturizing agents, vitamins and sunscreens, and mixtures thereof. The at least one additive may be present in the composition in an amount ranging from 0.01% to 10% relative to the total weight of the composition.

Needless to say, a person skilled in the art will take care to select the optional additional additives and/or the amount thereof such that the advantageous properties of the composition according to the present disclosure are not adversely affected by the envisaged addition, and for example such that the thermal profile of the composition remains as described above.

The cosmetic composition according to the present disclosure may be manufactured by the known processes generally used in cosmetics.

For instance, the cosmetic composition as disclosed herein may be intended to be heated. The heating of the composition may be performed before applying the product. To this end, the reservoir comprising the composition may, in the manner described in U.S. Pat. No. 5,775,344, be equipped with heating means arranged on the inner walls of the reservoir so as to heat the product it contains.

Alternatively, the heating may taken place via microwaves or a water bath, by using a device of the type described in U.S. Pat. No. 5,856,653.

The heating of the composition, for example, in order to curl the eyelashes, may be performed after applying the product, for example using devices as described in U.S. Pat. No. 5,853,010.

Figure 2:
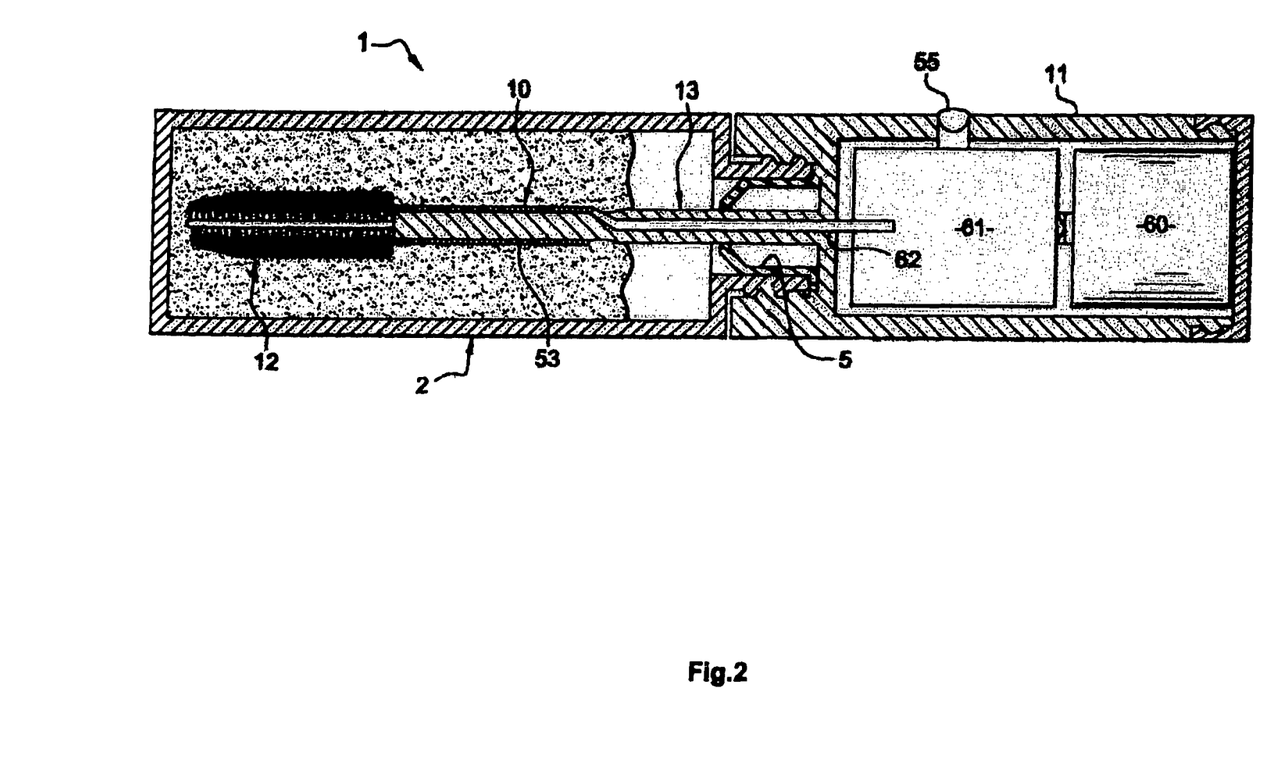
FIG. 2 shows a schematic representation of a device used to heat a mascara composition in accordance with the claims.

According to one aspect of the present disclosure, however, in the case where the composition as disclosed herein is an eyelash mascara, the application and heating may be performed in combination using a device as represented in FIG. 2.

Such a device comprises a device (1) in accordance with FIG. 2.

Inside the lid (11) is a DC power source (60), for instance in the form of a rechargeable battery, connected to control electronics (61). A switch in the form of a push button (55) allows the heating part (53) of the application device (10) to be selectively switched on and off. An LED is incorporated into the push button (55) and changes color when the composition contained in the reservoir (2) is at the appropriate temperature.

The lid (11) is solidly fastened to a stem (13), at the end of which is fixed a brush (12) of twisted brush type.

The control electronics are connected to a resistor (53) configured in the form of a coiled wire on the outer surface of the stem (13). The winding has connected coils and extends substantially from the end of the stem adjacent to the brush (12), to a portion of the stem located substantially at the free surface of the product inside the container prior to the first use of the device. Part of the stem located above the helical winding is not substantially heated. This is the case for example, for the portion of the stem located opposite the lip of the training member (5).

Between the portion wound on the stem (13), resistor (53) and the control circuit (61), the wires (62) pass inside the stem (13). Their diameter, on the order of a millimeter, is substantially greater than that of the heating resistor (53), such that they are not substantially heated on this portion. The inertia of the system is thus minimized. Similarly, due to the substantial absence of heating of the stem opposite the drainer, this drainer can be made of conventional material.

Thus, using the switch (55), the user switches on the heating of the resistor (53). This resistor is in contact with the product inside the container (2) and brings it to a temperature above its end melting temperature. Typically, the composition is heated to about 60° C.

When the temperature is reached, the LED of the switch (55) turns green. The user then unscrews the lid (11) and removes the applicator from the container (2).

During the removal action, the brush (12) is drained in a conventional manner. The product thus heated is then conventionally applied, by imposing on the eyelashes a motion intended to curl them.

Upon cooling, the cosmetic composition returns to its crystalline state, and may do so quickly due to the narrow width of the melting peak. The eyelashes are set, in a long-lasting manner, in the desired curled configuration.

Alternatively, the heating means are made for example, in the form of an incandescence lamp and are arranged inside a hollow member, the outer surface of which comprises application members, such as strips, teeth or bristles.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result. The percentages are given on a weight basis. The following examples are intended to illustrate the invention in a non-limiting manner.

EXAMPLE 1

A mascara having the composition below was prepared:

| | |
|---|---|
| Semi-crystalline polymer (polystearyl acrylate) | 23.3 g |
| Polybutene | 11.7 g |
| Stearic acid | 5.8 g |
| Aminopropanediol | 0.5 g |
| Hydroxyethylcellulose | 0.9 g |
| Gum Arabic | 3.45 g |
| Triethanolamine | 2.4 g |
| Pigments | 8 g |
| Preserving agents | qs |
| Water qs | 100 g |

Procedure

The semi-crystalline polymer and the polybutene were heated until melted and then placed under magnetic stirring.

The stearic acid, the aminopropanediol and pigments were added and the whole composition was heated on a water bath with stirring using a Moritz stirrer.

The water, the preserving agent, the hydroxyethylcellulose, the gum arabic and the triethanolamine were then added with rapid stirring to produce the emulsion.

Figure 1:
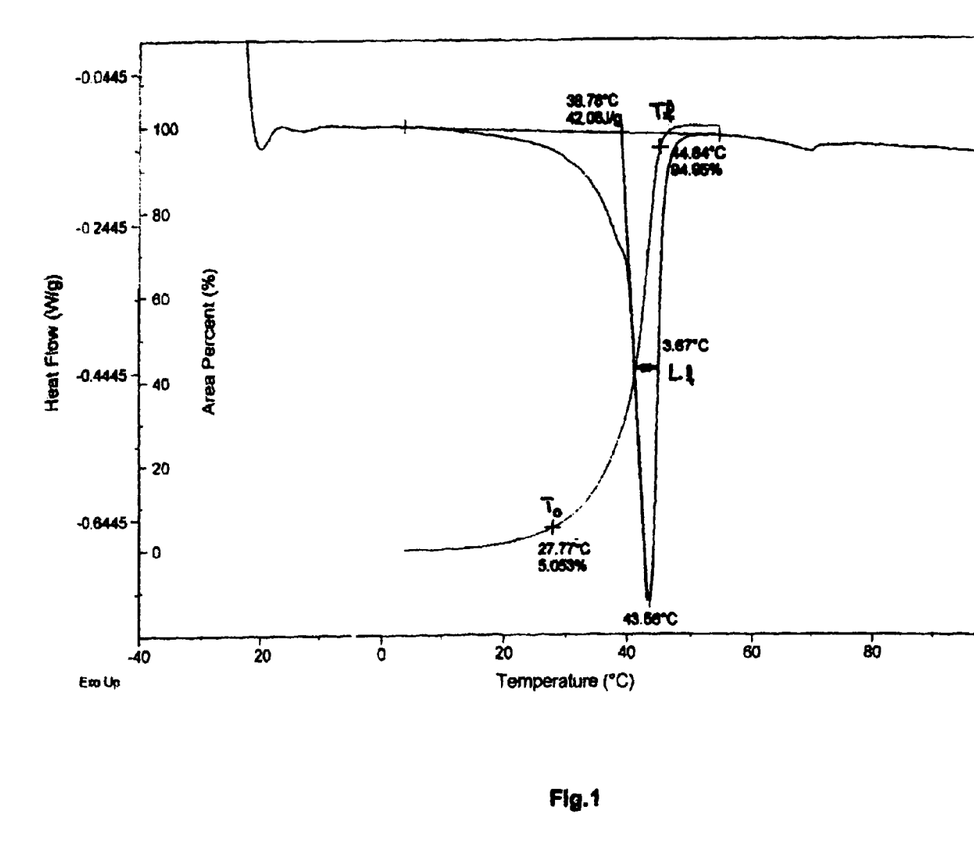
FIG. 1 shows a thermal profile obtained for a composition prepared in accordance with the claims.

This mascara composition had a thermal profile characterized by a melting peak as shown in FIG. 1.

It had the following parameters:
starting melting temperature To=27.77° C.
end melting temperature Tf=44.84° C.
melting amplitude ΔT=17.07° C.
mid-height peak width Lf=3.67° C.

The melting point of the composition was 43.56° C.

The heat stability of the composition was determined in the following manner:
the viscosity of the composition at To was determined,
the composition was placed in an oven at 80° C. for 2 hours and was then left to return to room temperature after removing it from the oven, which corresponds to one heating cycle. The operation was repeated several times, and the viscosity was measured at the end of each cycle using a Rheomat RM 180 viscometer equipped with an Ms-r3 or Ms-r4 spindle rotating at 240 min$^{-1}$ for a 60 Hz power supply or at 200 min$^{-1}$ for a 50 Hz power supply.

The following results were obtained:

It was found that this composition was able to regain its initial viscosity ±15% after several cycles of heating to a temperature above its melting point.

After applying the composition to the eyelashes and then heating the film of composition for a few seconds using a heating brush, this mascara was judged as allowing a significant improvement in the curling of the eyelashes.

What is claimed is:

1. A cosmetic composition comprising, in a non-toxic medium, polystearyl acrylate having a thermal profile having a melting peak wherein the mid-height width Lf is less than or equal to 20° C.,
wherein said thermal profile is determined by heating an empty crucible and a crucible containing a sample of said composition and measuring the variation of the difference in power absorbed by the empty crucible and by the crucible containing the sample as a function of temperature; and
wherein the cosmetic composition itself has a thermal profile having a melting peak wherein the mid-height width Lf is less than or equal to 20° C.,
and wherein the cosmetic composition further comprises a film-forming polymer selected from:
synthetic polymers resulting from the radical-mediated polymerization of at least one monomer selected from acrylic acid, methacrylic acid, methyl methacrylate, butyl methacrylate, 2-ethylhexyl methacrylate, hydroxyethyl acrylate, hydroxyethyl methacrylate, 2-hydroxypropyl acrylate, and 2-hydroxypropyl methacrylate;
gum arabic;
polyurethanes;
polyesters;
aqueous dispersions of polymers selected from acrylic, polyurethane, and hybrid polymers;
polymers of cellulose selected from hydroethylcellulose, hydroxypropylcellulose, methylcellulose, and carboxymethylcellulose;
polyvinylpyrrolidones;
polyurethane-polyvinylpyrrolidones; and
copolymers of vinyl pyrrolidone and of caprolactam; copolymers of vinylpyrrolidone and of vinyl acetate; copolymers of vinylpyrrolidone and of ethyl methacrylate; butylated polyvinylpyrrolidine; copolymers of vinylpyrrolidone and of eicosene; copolymers of vinylpyrrolidone and of hexadecene; copolymers of vinylpyrrolidone and of triacontene; and copolymers of vinylpyrrolidone and of styrene.

2. The cosmetic composition according to claim 1, wherein the melting peak of the cosmetic composition has a starting melting temperature To of greater than or equal to 10° C.

| | at To | After 1 heating cycle | After 2 heating cycles | After 3 heating cycles | After 4 heating cycles | After 10 heating cycles | After 15 heating cycles |
|---|---|---|---|---|---|---|---|
| Viscosity (Pa.s) | 6.7 | 7.4 | 7.2 | 7.7 | 7.6 | 7.2 | 7.1 |
| Variation in viscosity, in % | | 10 | 7.5 | 14.9 | 13.4 | 7.5 | 5.9 |

3. The cosmetic composition according to claim 2, wherein the starting melting temperature To of the cosmetic composition is greater than or equal to 15° C.

4. The cosmetic composition according claim 1, wherein the melting peak of the cosmetic composition has an end melting temperature Tf of less than or equal to 90° C.

5. The cosmetic composition according claim 4, wherein the end melting temperature Tf of the cosmetic composition is less than or equal to 80° C.

6. The cosmetic composition according to claim 5, wherein the end melting temperature Tf of the cosmetic composition is less than or equal to 70° C.

7. The cosmetic composition according to claim 1, wherein the melting peak of the cosmetic composition has a melting point ranging from 20° C. to 80° C.

8. The cosmetic composition according to claim 1, wherein the mid-height width Lf of the cosmetic composition is less than or equal to 10° C.

9. The cosmetic composition according to claim 1, wherein the melting peak of the cosmetic composition has a temperature amplitude, ΔT, Tf–To, of less than or equal to 30° C.

10. The cosmetic composition according to claim 1, further comprising an aqueous phase.

11. The cosmetic composition according to claim 1, further comprising at least one dyestuff.

12. A non-therapeutic cosmetic process for making up a keratin material, comprising applying to the keratin material a cosmetic composition according to claim 1.

13. A process for coating keratin fibers in order to deposit a film on said keratin fibers, wherein the film is homogenous and/or has improved curling properties, said process comprising applying to the fibers a cosmetic composition according to claim 1.

14. The cosmetic composition according to claim 1, wherein the film-forming polymer is selected from:
  synthetic polymers resulting from the radical-mediated polymerization of at least one monomer selected from acrylic acid, methacrylic acid, methyl methacrylate, and hydroxyethyl acrylate;
  gum arabic;
  polyurethanes;
  polyesters;
  aqueous dispersions of polymers selected from acrylic, polyurethane, and hybrid polymers;
  polymers of cellulose selected from hydroethylcellulose, hydroxypropylcellulose, methylcellulose, and carboxymethylcellulose;
  polyvinylpyrrolidones;
  polyurethane-polyvinylpyrrolidones; and
  copolymers of vinyl pyrrolidone and of caprolactam; copolymers of vinylpyrrolidone and of vinyl acetate; copolymers of vinylpyrrolidone and of ethyl methacrylate; butylated polyvinylpyrrolidone; copolymers of vinylpyrrolidone and of eicosene; copolymers of vinylpyrrolidone and of hexadecene; copolymers of vinylpyrrolidone and of triacontene; and copolymers of vinylpyrrolidone and of styrene.

15. The cosmetic composition according to claim 1, wherein the film-forming polymer is selected from:
  synthetic polymers resulting from the radical-mediated polymerization of methacrylic acid;
  gum arabic; and
  aqueous dispersions of polymers selected from acrylic, polyurethane, and hybrid polymers.

16. The cosmetic composition according to claim 1, wherein the film-forming polymer is polyvinylpyrrolidone.

* * * * *